(12) United States Patent
Schröter (10) Patent No.: US 11,007,065 B2
(45) Date of Patent: May 18, 2021

(54) PREVENTION OF VERTEBRAL IMPLANT COMPRESSION

(71) Applicant: ulrich GmbH & Co.KG, Ulm (DE)

(72) Inventor: Martin Schröter, Weißenhorn (DE)

(73) Assignee: ulrich GmbH & Co.KG, Ulm (DE)

( * ) Notice: Subject to any disclaimer, the term of this patent is extended or adjusted under 35 U.S.C. 154(b) by 0 days.

(21) Appl. No.: 16/316,787

(22) PCT Filed: Aug. 11, 2017

(86) PCT No.: PCT/EP2017/070485
§ 371 (c)(1),
(2) Date: Jan. 10, 2019

(87) PCT Pub. No.: WO2018/029357
PCT Pub. Date: Feb. 15, 2018

(65) Prior Publication Data
US 2019/0151108 A1  May 23, 2019

(30) Foreign Application Priority Data

Aug. 11, 2016  (LU) .......................................... 93170

(51) Int. Cl.
*A61F 2/44*  (2006.01)
*A61F 2/46*  (2006.01)
*A61F 2/30*  (2006.01)

(52) U.S. Cl.
CPC ............ *A61F 2/442* (2013.01); *A61F 2/4611* (2013.01); *A61F 2002/302* (2013.01); *A61F 2002/3009* (2013.01); *A61F 2002/3055* (2013.01); *A61F 2002/30235* (2013.01); *A61F 2002/30405* (2013.01); *A61F 2002/30579* (2013.01); *A61F 2002/30593* (2013.01); *A61F 2002/30604* (2013.01); *A61F 2002/4627* (2013.01)

(58) Field of Classification Search
CPC ................................................. A61F 2/44–447
See application file for complete search history.

(56) References Cited

U.S. PATENT DOCUMENTS

| 6,524,341 B2 * | 2/2003 | Lang ........................ A61F 2/44 623/17.15 |
| 7,641,693 B2 * | 1/2010 | Gutlin ...................... A61F 2/44 623/17.15 |
| 7,776,091 B2 * | 8/2010 | Mastrorio .......... A61B 17/7065 623/17.15 |
| 8,197,546 B2 * | 6/2012 | Doubler .................... A61F 2/44 606/279 |
| 8,282,683 B2 * | 10/2012 | McLaughlin ......... A61F 2/4455 623/17.11 |

(Continued)

*Primary Examiner* — Eduardo C Robert
*Assistant Examiner* — Steven J Cotroneo
(74) *Attorney, Agent, or Firm* — 24IP Law Group USA, PLLC; Timothy R. De Witt (57) ABSTRACT

The present invention relates to a safety element, an implant comprising such a safety element and an implant system comprising an implant with the safety element. The safety element for an implant is arranged between an outer and inner part of an implant, wherein the safety element engages into the gearing of an expansion ring, wherein a releasing space between outer part and inner part of the implant is provided into that the safety element is to be radially moved for enabling rotation of the expansion ring.

11 Claims, 5 Drawing Sheets

(56) References Cited

U.S. PATENT DOCUMENTS

| | | | | |
|---|---|---|---|---|
| 8,721,723 B2* | 5/2014 | Hansell | ................... | A61F 2/442 623/17.15 |
| 9,301,850 B2* | 4/2016 | McLaughlin | ........... | A61F 2/446 |
| 9,474,621 B2* | 10/2016 | McLaughlin | .......... | A61F 2/4465 |
| 2007/0191954 A1* | 8/2007 | Hansell | ................... | A61F 2/442 623/17.15 |
| 2011/0178598 A1* | 7/2011 | Rhoda | ..................... | A61F 2/442 623/17.16 |
| 2011/0218631 A1* | 9/2011 | Woodburn, Sr. | ........ | A61F 2/442 623/17.16 |
| 2012/0265303 A1* | 10/2012 | Refai | ................... | A61F 2/4465 623/17.11 |
| 2013/0331943 A1* | 12/2013 | Arnold | ................. | A61F 2/4611 623/17.15 |
| 2015/0018957 A1 | 1/2015 | Nichols | | |
| 2016/0100955 A1* | 4/2016 | Stinchfield | ............ | A61F 2/4465 623/17.15 |

* cited by examiner

PREVENTION OF VERTEBRAL IMPLANT COMPRESSION

FIELD OF THE INVENTION

The present invention relates to a vertebral implant.

BACKGROUND OF THE INVENTION

Different intervertebral disc prostheses for substitution of the intervertebral disc are known today. Function-retaining disc implants are used avoid fusion surgery, i.e. to maintain or restore mobility within the intervertebral disc space. Such prostheses comprise at least an upper and a lower plate, for firm fixation with the upper and lower vertebra neighbouring the intervertebral space into which the prostheses shall be placed. Those two plates do not only represent so called end plates, but may also comprise at least one sliding area or articulation area formed by their inner surfaces. At least one sliding area has to be present within a prosthesis in order to allow motion of neighbouring parts and thus of the vertebra connected to the send plates of the prosthesis.

An intervertebral disc prosthesis may also serve a different purpose, namely to retain the distance of vertebra due to removal of a degenerated or damaged intervertebral disc. The prior art discloses several solutions for this purpose like expandable cages or other at least partly hollow devices which may be filled with bone cement for their stabilization.

Vertebral implants are known besides intervertebral disc prosthesis. Such implants are used to substitute a vertebral body. This means, that the implant has to span the space between the neighboring vertebral bodies of the one that has to be substituted.

Document U.S. Pat. No. 8,721,723 B2 discloses an expandable prosthetic implant device for engagement between vertebrae. The implant comprises two members which are movable relative to each other in their longitudinal axis. In order to avoid unintended movement of the two members, a locking assembly is provided having a flexible member positioned between the inner member and the outer member and movable between a first position and a second position, and wherein in the first position one end of the flexible member engages with one of a plurality of notches configured on an inner surface of the gear member to block movement of the gear member, and in the second position the flexible member is disengaged from one of the plurality of notches and allows movement of the gear member which allows relative movement between the inner member and the outer member.

The published patent application US 2007/0191954 A1 relates to an expandable prosthetic implant device for engagement between vertebrae generally comprising an inner member, outer member, and gear member positioned coaxial with respect to each other such that the inner and outer members are moveable relative to each other along an axis. The gear member is axially fixed to the outer member and freely rotatable with respect to the outer member and the gear member threadedly engages a threaded portion of the inner member to translate inner member along the axis. The implant is configured to engage the vertebrae in a predetermined alignment and the gear member includes gear teeth exposed to the exterior and configured to be accessible by a tool member at a plurality of angular positions around the perimeter of the implant device. Movement is blocked by providing locking member spaced around the periphery of the outer member, wherein the locking member engage into vertical slots of the inner member. The locking member of a device according to US 2007/0191954 A1 is disadvantageous in making the prosthetic implant more complex by providing additional parts with the locking member and the vertical slots within the inner member.

Document US 2015/0018957 A1 discloses tissue spacer implants and surgical methods for inserting such implants. The implants of this document include a first cylindrical body with an outer surface, an axially extending hole, and a first end, a second cylindrical body with an outer surface and an axially extending hole, and an adjustment member with an outer surface, an axial hole, and at least one helical slot. The adjustment member axial hole may be adapted to receive the first cylindrical body and the adjustment member may be configured to be inserted into the axially extending hole of second cylindrical body. The implants may also include a travel mechanism for engaging the first cylindrical body, adjustment member, and second cylindrical body along the at least one helical slot to maintain a space between two bodies of tissue. Unintended movement of an intermediate adjustment member is avoided by tightening a nut. The disclosed locking mechanism for unintended movement of the implant's parts has the disadvantage of being very complex in handling, e.g. during surgery, even when taking necessary adjustments of the implant's height into account after the implant has already been inserted.

It is important to avoid unintended changes in height of the prosthesis. For that reason, means have to be provided which allow to adapt the height of the prosthesis to the respective intervertebral space, but also to block any unintended movement of parts that may change the height of the prosthesis. In particular, any compression of the implant due to a changing or increasing load onto the prosthesis has to be avoided.

Thus, there is a need for an intervertebral disc prosthesis for the cervical and lumbar spine that enables easy adaptation of the height of the prosthesis while providing means to prevent compression or any unintended change of the height.

SUMMARY OF THE INVENTION

The present disclosure provides a safety element for an implant, arranged between an outer and inner part of an implant; the safety element engaging into the same gearing of an expansion ring, which is used for actuating the expansion ring, wherein a releasing space between outer part and inner part of the implant is provided into that the safety element is to be radially moved for enabling rotation of the expansion ring.

The safety element may be accessible from the outside through an opening in the outer part.

The shape of the part of the safety element engaging into the gearing shall correspond to the shape of the gearing of the expansion ring.

The safety element may be fixed to the inner surface of the outer part.

It is further intended that the safety element is a flat spring.

Another object of the present invention is an implant for fixation between vertebra, wherein the implant comprises an outer part for accommodating an inner part, wherein outer part and inner part are movable relative to another; wherein an expansion ring with a thread on its inner side engages into a thread on the outer side of the inner part, wherein the expansion ring is coaxially fixed to the outer part and further comprises a gearing on its upper or lower side; wherein the implant comprises a safety element as described above.

The outer part of the implant may be a hollow cylinder and the expansion ring may be pivoted into a collar of the outer member, wherein the collar is arranged at the upper end of the outer part.

The outer part of the implant may have a recesses for accommodating a holder profile of an expansion tool.

The implant may further have an upper end plate for fixation to an upper vertebra that is fixed at the upper end of the inner part and the lower end of the outer part is adapted for fixation to a lower vertebra or comprises a lower end plate.

The implant may comprise at least one radiolucent tag.

The upper end plate of an implant may be firmly, but re-movably fixed to the inner part.

A further object of the instant invention is an implant system for the total replacement of an intervertebral disc, comprising an expandable implant and a safety element as described above in addition to an expansion tool having a holder profile for engaging into an outer recess of the outer part of the expandable prosthesis, wherein the expansion tool has a centrally located shaft within the holder profile for radial movement of the safety element into a space between outer and inner part of the prosthesis, wherein the shaft has a gearing on its outer surface engaging into the gearing of the expansion ring so that the expansion ring can be rotated by rotation of the shaft within the expansion tool.

The expansion tool of the system may have a grip connected via a gearing to the shaft so that rotation of the grip causes rotation of the shaft.

The system may further provide that the expansion tool has a grip connected via a gearing to the shaft so that rotation of the grip causes rotation of the shaft.

BRIEF DESCRIPTION OF THE FIGURES

The present invention will be described by figures and examples. It is obvious for a person ordinary skilled in the art that the scope of the invention is not limited to the disclosed embodiments. It shows.

DETAILED DESCRIPTION OF THE INVENTION

The prosthesis provided by the invention is intended for primary total disc replacement allowing adjustment of the height of the prosthesis.

Within the meaning of the instant disclosure the term prosthesis or implant shall be understood synonymously.

The three spatial axes shall be defined as "sagittal rotational axis" for the extension and flexion function within the disc space, going from the front to the back through the body or vice versa. The rotation around the sagittal axis is in the dorsal and ventral (dorso-ventral) direction. The bending function to the right and left side of the disc space is performed around the "frontal rotational axis" going from the right to the left of the body or vice versa. The "longitudinal axis" is for the right/left axial rotation, meaning the rotation around the vertical axis running in cranio-caudal direction of the body. This rotation is also designated as "axial rotation".

The term "frontal" is synonymous with "ventral" and "anterior" and the term "back" with "dorsal" and "posterior". A "frontal section" or the "frontal view" is a vertical section from the right lateral side to the left lateral side of a body or vice versa.

A gearing within the meaning of the present invention designates a toothing that is used for actuating a part, like the gearing of the expansion ring.

The implant of the instant disclosure can be expanded by screwing the inner part within the outer part with the attached expansion ring. In order to avoid unintended movement between inner part and expansion ring, the safety element engages into the same gearing of the expansion ring, which is also used for actuating the expansion ring. Thus, the gearing of the expansion ring has a double function: A use for actuating the expansion ring and its use for blocking movement of the expansion ring.

The safety element is spring loaded so that it will be in a blocking position without its active movement into a releasing position. The safety element is for that reason a flat spring that is fixed to the outer member.

The space between inner and outer part is adjusted to the thickness or material thickness of the safety element. It is also within the scope of the present disclosure if the inner part has a circular recess for providing a space for the releasing position of the safety element.

Since the prosthesis of the present disclosure is related to rotation in order to change its the height a cylindrical form of outer and inner part is beneficial.

The safety element has to be actively moved radially into its releasing position. Thus, there has to be an opening allowing access to the safety element in its blocking position. It is obvious for a person having ordinary skill in the art that the use of a gearing on the upper or lower side of the expansion ring is advantageous, because the force that will be applied to the blocking element, respectively the expansion ring is directly located on the radial axis of movement of the expansion ring.

The use of a gearing on the upper or lower side of the expansion ring is for that reason advantageous in comparison to the measures disclosed in U.S. Pat. No. 8,721,723 B2, where the force for blocking movement of the gear member is exerted vertically to the disclosed notches. The load of blocking the gear member of U.S. Pat. No. 8,721,723 B2 is exerted onto the notches and not onto the gear member itself. A further advantage of the present invention is that only one gearing is necessary for actuating and blocking movement of the expansion ring instead of providing a further toothing for blocking its movement.

The shapes of the gearing or the teeth of the gearing and the end of the safety element engaging into the gearing correspond in order to optimize distribution of the blocking force.

The fixation of the expansion ring to the outer part simply has to allow rotation of the expansion ring, which is fixed as regards movement out of the outer part. It is also within the scope of the present disclosure if the expansion ring is not located at the upper end of the outer part, but within the outer part.

The upper end of the inner part may have an end plate that can be adapted to shape and size of the upper vertebra to which it shall be fixed. The upper surface of the end plate may have means for anchoring within the vertebra like teeth or a bioactive coating. Accordingly, the lower end of the outer part may be adapted and provide means for fixation to a lower vertebra.

The outer part of an expandable prosthesis may provide means like holes or recesses to enable an expansion tool to engage firmly with the prosthesis. A recess or hole may be circular or rectangular or a combination thereof to enable a safe contact between both partners without unnecessary tolerance.

The end plate connected to the upper end of the inner part may be movably connected allowing a dorsoventral and/or lateral movement of the part of the prosthesis with regard to another. Such measures allow for retaining movement of the connected vertebra of the vertebral space into which the prosthesis will be implanted. According measures are intended for the lower end of the outer part.

The fixation of end plates may also provide for rotational movement of the parts of the prosthesis and thus of the connected vertebra. In case that movement will be allowed between part of the prostheses, edges may be provided to ensure that punctual contacts between parts of the prosthesis will be avoided.

An end plate may be fixed firmly, but reversibly so that the expandable part of the prosthesis may be exchanged during reversion surgery.

The disclosed expandable prosthesis may also be part of an implant system as described above. The system provides an expansion toll that is suitable to move the safety element into a releasing position by inserting a shaft pressing the safety element radially into the space provided between outer and inner part.

In addition, the shaft has a gearing on its outer surface that engages and corresponds to the gearing of the expansion ring. By rotating the shaft, the expansion ring will rotate around its center. Due to the thread of the expansion ring that engages into the thread on the outer surface of the inner part, the height of the prosthesis will change.

Outer part, inner part, expansion ring and safety element form the expandable part of a prosthesis according to the instant disclosure.

The shaft of the expansion tool may be rotated via a gearing connecting is to the grip of the expansion tool. It is an advantage of the present invention that no extra tool is necessary for handling safety parts necessary for locking the prosthesis against unintended movement.

Figure 1:
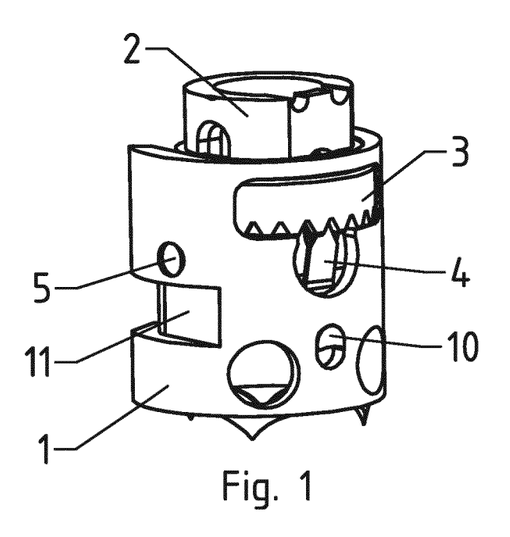
FIG. 1 Overview of an implant

FIG. 1 shows an overview of an implant with inner part 2 which is arranged within outer part 1. The expansion ring 3 is prevented from radial movement by safety element 4 engaging into the gearing of expansion ring 3.

Figure 2:
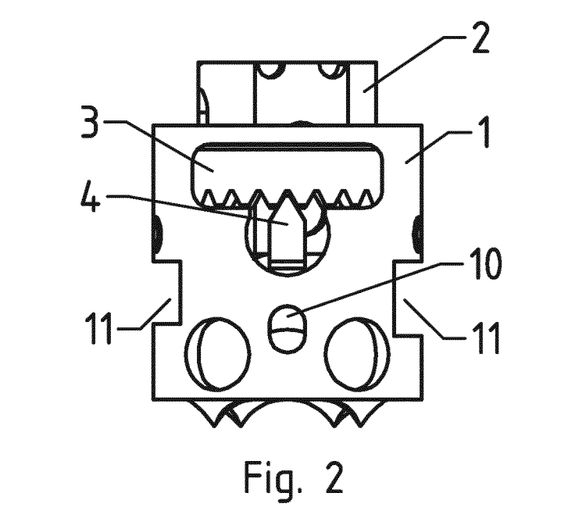
FIG. 2 View onto implant with expansion ring and safety element

FIG. 2 shows a view onto the inner part 2 and the outer part 1 of the implant with expansion ring 3 and safety element 4. The safety element is fixed to the outer part 1 with fixation 10 which fits into a hole of the outer part 1. Guiding grooves 11 for taking up the guiding of an expansion tool (not shown) are arranged on the sides of the outer part 1.

Figure 3:
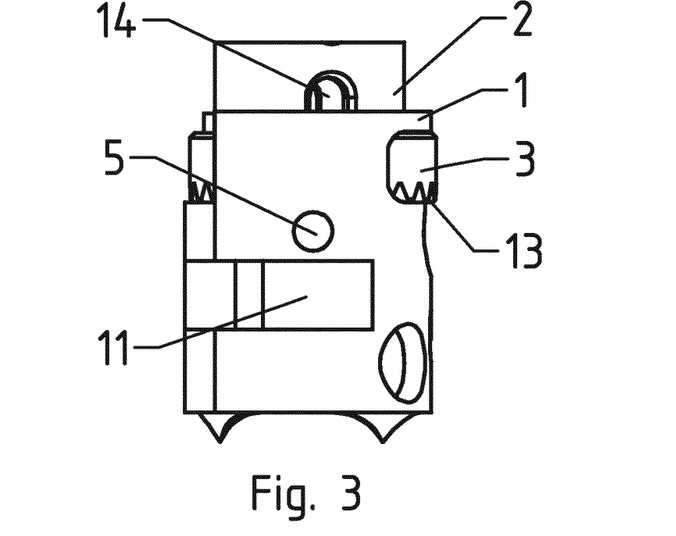
FIG. 3 Side view onto the implant

FIG. 3 shows a side view onto the implant with outer part 1 and inner part 2 arranged within outer part 1. The location of expansion ring 3 with gearing 13 between inner part 2 and outer part 1 is visible. Guiding bolts 5 engaging into guiding slit 14 can be seen. Interaction of guiding bolts 5 and guiding slit 14 prevent the inner part 2 from rotation during extraction.

Figure 4:
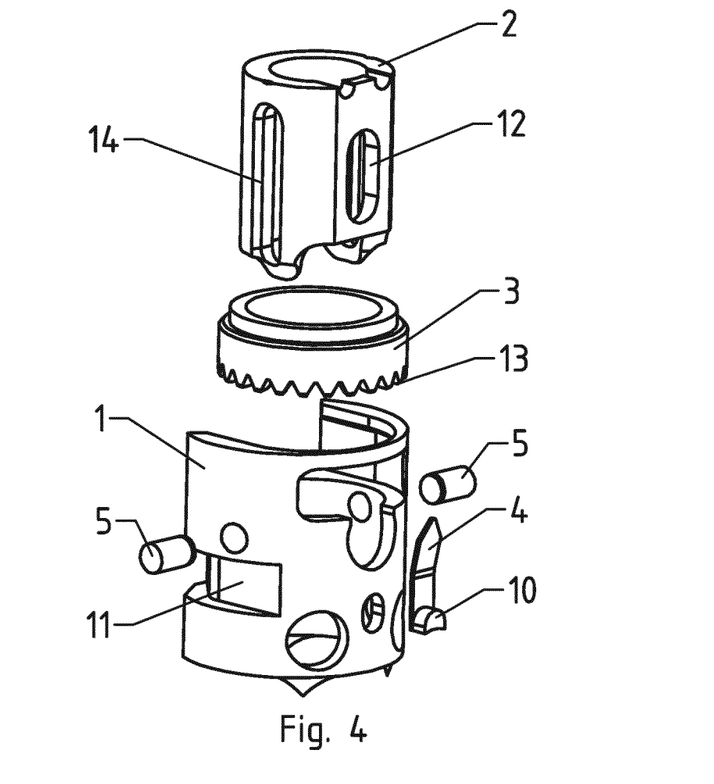
FIG. 4 Exploded view onto an implant with safety element

FIG. 4 shows an exploded view onto an implant with safety element 4. The inner part 2 has a releasing space 12 for taking up safety element 4 to release expansion ring 3 so that it can be rotated radially. The releasing space 12 may result from a flattened ventral part of the inner part 2 so that the cross section of the inner part is not completely round. Expansion ring 3 has a gearing 13 on its lower side into which safety element 4 engages with its upper end. The shape of the upper end of the safety element 4 corresponds to the shape of gearing 13 of the expansion ring.

The outer part 1 has guiding grooves 11 on each side. Guiding bolts 5 are arranged within holes at both sides of the outer part 1. The safety element is fixed by affixation 10 arranged at the lower end of safety element 4 accommodating into a hole of the outer part 1. The upper part of the safety element 4 is bent outwardly for engaging into the gearing 13 of expansion ring 3 to block radial rotation.

Figure 5:
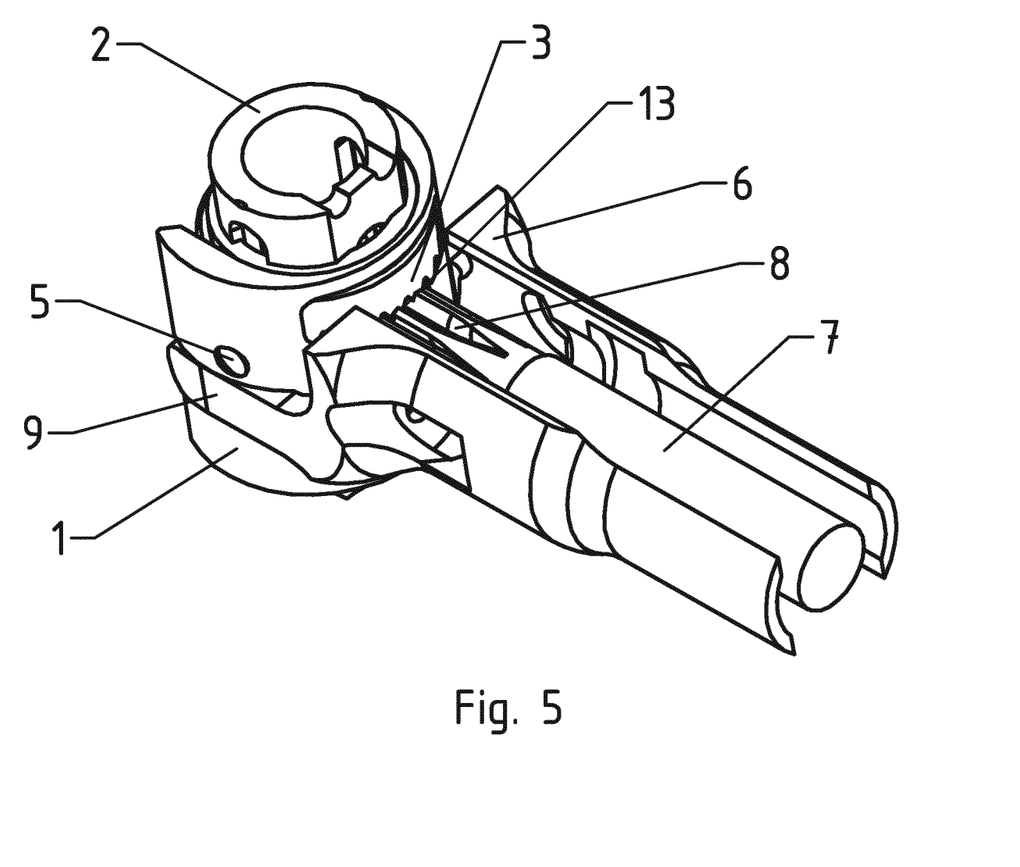
FIG. 5 Overview onto an implant system with expansion tool

FIG. 5 shows an overview onto an implant system with expansion tool 6. The implant is shown with outer part 1 and inner part 2. The guiding of the expansion tool engages into guiding grooves of the outer part 1. The gearing 8 of shaft 7 engages into gearing 13 of expansion ring 3. Guiding bolts 5 are also depicted.

Figure 6:
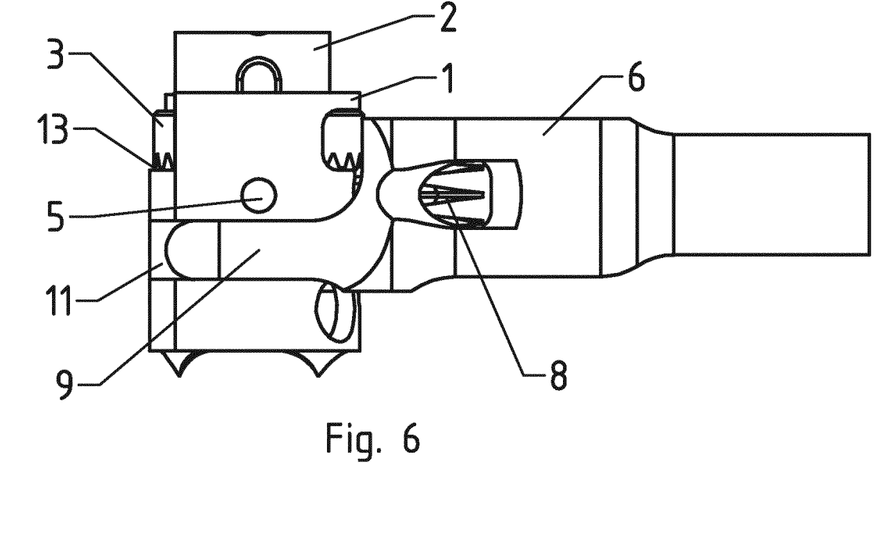
FIG. 6 Side view onto implant system with expansion tool

FIG. 6 shows a side view onto an implant system with expansion tool 6. This figure shows guiding of the expansion tool by the interaction between guiding 9 of the expansion tool 6 engaging into guiding grooves 11 of the outer part 1. Gearing 8 of the expansion tool 6 engages into gearing 13 of the expansion ring 3. The safety element 4 is pressed into the releasing space for enabling radial movement of the expansion ring to expand or compress the implant by movement of inner part 2 (not shown).

Figure 7:
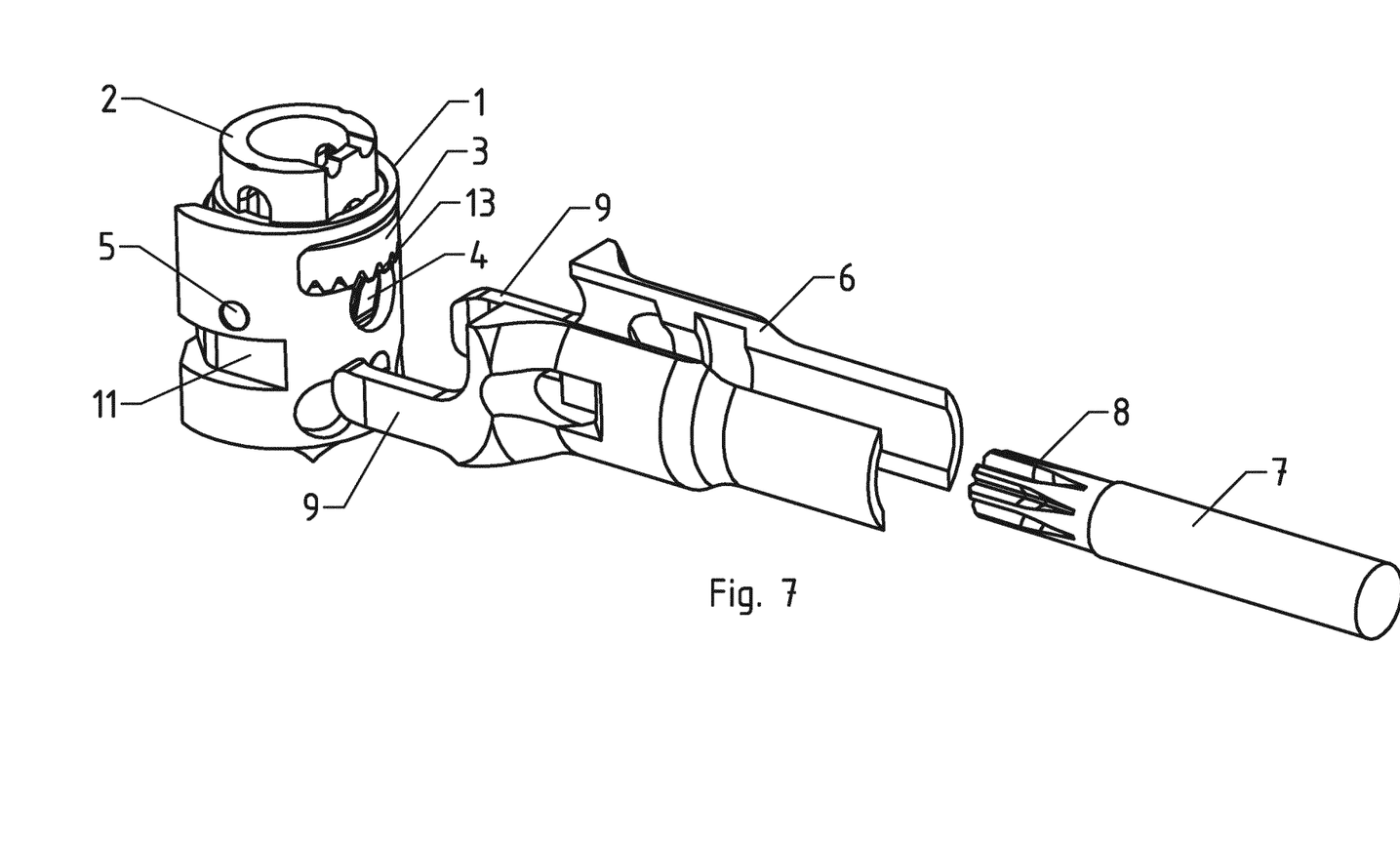
FIG. 7 Implant with exploded expansion tool

FIG. 7 shows the implant system in an exploded view. The expansion tool 6 comprises to parts enclosing shaft 7 with gearing 8 on the tip, which is pressing safety element 4 into the releasing space (not shown). Interaction between guiding 9 with guiding grooves 11 ensures correct positioning of the expansion tool 6. Shaft 7 with gearing 8 fulfills two purposes: (i) releasing the expansion ring 3 by pressing safety element 4 into the releasing space and radially moving expansion ring 3 by rotation of shaft 7.

REFERENCE NUMERALS 1 outer part
2 inner part
3 expansion ring
4 safety element
5 guide bolts
6 expansion ring
7 shaft
8 gearing of shaft
9 guiding of expansion tool
10 fixation safety element
11 guiding groove
12 releasing space
13 gearing expansion ring

The invention claimed is:

1. An implant for fixation between vertebrae, wherein the implant comprises an outer part for accommodating an inner part, wherein the outer part and the inner part are movable relative to another; wherein an expansion ring with a thread on its inner side engages into a thread on an outer side of the inner part, wherein the expansion ring is coaxially fixed to the outer part and further comprises a gearing on its upper or lower side extending from an inner expansion ring surface to an outer expansion ring surface for actuating the expansion ring; wherein a safety element, which is a flat spring, is arranged between said outer and inner part engaging into the same gearing of the expansion ring, which is used for actuating the expansion ring, wherein a releasing space between outer part and inner part of the implant is provided into that the safety element radially moves for enabling rotation of the expansion ring.

2. The implant of claim 1, wherein the outer part is a hollow cylinder.

3. The implant of claim 1, wherein the expansion ring is pivoted into a collar of the outer part.

4. The implant of claim 3, wherein the collar is arranged at an upper end of the outer part.

5. The implant of claim 1, wherein the outer part has a recess for accommodating a holder profile of an expansion tool.

6. The implant of claim 1, wherein an upper end plate for fixation to an upper vertebra is fixed at the upper end of the inner part and the lower end of the outer part is adapted for fixation to a lower vertebra or comprises a lower end plate.

7. The implant of claim 1, wherein the implant comprises at least one radiolucent tag.

8. The implant of claim 1, wherein an upper end plate is firmly, but removably fixed to the inner part.

9. An implant system for the total replacement of an intervertebral disc, comprising an expandable implant of claim 1 and a expansion tool having a holder profile for engaging into an outer recess of the outer part of the expandable implant, wherein the expansion tool has a centrally located shaft within the holder profile for radial movement of the safety element into a space between outer and inner part of the implant, wherein the shaft has a gearing on its outer surface engaging into the gearing of the expansion ring so that the expansion ring can be rotated by rotation of the shaft within the expansion tool.

10. The system of claim 9, wherein the expansion tool has a grip connected via a gearing to the shaft so that rotation of the grip causes rotation of the shaft.

11. An implant for fixation between vertebrae, the implant comprising:
    an inner part;
    an outer part;
    a releasing space between the outer part and the inner part;
    an expansion ring having a gearing on its upper or lower side extending from an inner expansion ring surface to an outer expansion ring surface configured to actuate the expansion ring; and
    a safety element arranged between the outer part and inner part of the implant;
    wherein the safety element engages into the gearing of the expansion ring; and
    wherein the releasing space between outer part and inner part of the implant is configured to require that the safety element is to be radially moved to enabling rotation of the expansion ring.

* * * * *